United States Patent [19]

Elston et al.

[11] 4,343,765
[45] Aug. 10, 1982

[54] METHOD FOR DEODORIZING AND DISINFECTING AIR

[75] Inventors: Lewis W. Elston, Atlanta; David R. Hurst, Norcross, both of Ga.

[73] Assignee: Georgia Tech Research Institute, Atlanta, Ga.

[21] Appl. No.: 215,269

[22] Filed: Dec. 11, 1980

[51] Int. Cl.³ .............................................. A61L 9/015
[52] U.S. Cl. .......................................... 422/3; 422/4; 422/31; 422/37; 422/122
[58] Field of Search ....................... 422/3, 4, 5, 37, 31, 422/122; 62/78

[56] References Cited

U.S. PATENT DOCUMENTS

| 1,961,878 | 6/1934 | Gilkey . | |
| 3,352,628 | 11/1967 | Starbuck | 422/4 |
| 3,421,836 | 1/1969 | Sundin et al. . | |
| 3,547,576 | 12/1970 | Sheikh . | |
| 3,969,479 | 7/1976 | Lonnes et al. . | |
| 4,256,710 | 3/1981 | Azuma et al. | 422/4 X |
| 4,256,728 | 3/1981 | Nishino et al. | 422/4 |

FOREIGN PATENT DOCUMENTS

| 197811 | 11/1978 | Fed. Rep. of Germany | 422/4 |
| 54-109069 | 8/1979 | Japan | 422/4 |
| 55-34137 | 3/1980 | Japan | 422/4 |
| 55-91359 | 7/1980 | Japan | 422/5 |

*Primary Examiner*—Barry S. Richman
*Attorney, Agent, or Firm*—Newton, Hopkins & Ormsby

[57] ABSTRACT

In a first embodiment of the method and apparatus, the oxidant is loaded upon a support bed and is continuously regenerated by an ozone generator located upstream from the support bed. The ozone generator has a capacity less than the peak load requirement for the oxidant but fully regenerates the oxidant during low load periods. An ozone detector is located downstream from the support bed and includes a control circuit for selectively deactivating the ozone generator when the ozone downstream from the support bed exceeds a predetermined level. The support bed is composed of inert or adsorbing granular material. In a second embodiment, an aqueous solution containing a water soluble oxidant is applied to the support bed and is rinsed out following a purification cycle. The rinsed oxidant is replaced by fresh oxidant from a reservoir and the rinsed, spent oxidant is regenerated in an electrolytic or chemical regenerator and returned to the oxidant reservoir. Parallel, alternatively operated, conduit sections including support beds therein may be provided so that one conduit section is operative to purify air flow while the other conduit section is being regenerated.

2 Claims, 3 Drawing Figures

METHOD FOR DEODORIZING AND DISINFECTING AIR

BACKGROUND OF THE INVENTION

1. Field of the Invention

The present invention relates to a method for removing offensive odors and infectious agents from recirculating building air, and an apparatus for carrying out the method, thereby increasing comfort within the building, reducing the need for make up air and reducing the energy required for the heating and cooling of the building.

2. Brief Description of the Prior Art

Many attempts have been made to remove offensive odors and infectious agents from buildings or rooms. The older methods include liquid and spray cleaning disinfecting agents. Liquid, solid, and spray odor masking agents have also been used for removing offensive odors and infectious agents from air. Other known methods includes activated carbon filters, and "one shot" oxidant impregnated or coated granules such as "Purafil", which consists of alpha alumina granules impregnated with potassium permanganate.

An example of a known method utilizing a cleaning and disinfecting agent may be found in U.S. Pat. No. 3,547,576 to Sheikh, which discloses an air sterilization process in which iodine crystals are volatilized and incorporated into air so as to kill bacterial organisms therein. Thereafter, washing the air mixtures with an iodine holding liquid captures the iodine in the air mixtures. A number of other known masking agents contain formaldehyde to deaden the sense of smell. However, in general, the scent of these commercial cleaning and odor masking agents is more offensive and irritating than the odor they eliminate or conceal. Further, the application of such commercial cleaner and odor masking agents also requires extensive labor in the frequent application thereof.

Activated carbon filters are effective in removing offensive odors, but the adsorbed organic material supplies an excellent substrate for the growth of infectious agents such as bacteria, fungi and viruses. Accordingly, the use such of filters, alone, has been found to be unsatisfactory.

Oxidant impregnated materials such as "Purafil" are effective in controlling odors. However, the oxidant becomes spent with use and accordingly, these granules are useable for a limited time period and must be replaced periodically (i.e., "one shot" use). The use of oxidizing agents for odor control on a continuous basis with recirculation of the oxidizing agent has been known, such as is described in U.S. Pat. No. 3,969,479, Lonnes et al. However, such methods also fail to provide for the regeneration of the spent oxidant and accordingly are also essentially "one shot" oxidizing methods.

It has also been known to utilize ozone for the purpose of purifing air (see U.S. Pat. No. 1,961,878 and U.S. Pat. No. 3,421,836). However, the introduction of ozone into the air in sufficient quantity to be effective as a disinfecting agent will also result in an unpleasant ozone odor which can be offensive to many people.

Accordingly, none of the prior art methods or apparatus for cleaning and disinfecting air can be used on a continuous basis without the need for frequent replenishment of the freshening agent, and without introducing unpleasant odor into the air being purified.

SUMMARY OF THE INVENTION

It is an object of the present invention to provide a method for deodorizing and disinfecting air.

It a further object of the present invention to provide a method for deodorizing and disinfecting air without the introduction of additional unpleasant odors to the air being purified.

It is a further object of the present invention to provide a method for deodorizing air by use of an oxidant.

It is a further object of the present invention to provide a method for deodorizing and disinfecting air by use of an oxidant which may be regenerated.

It is a further object of the present invention to provide a method for deodorizing and disinfecting air by the use of an oxidant which is regenerated in situ.

It is a further object of the present invention to provide a method for deodorizing and disinfecting air by the use of an oxidant which is dissolved in an aqueous solution and which is regenerated off-line.

It is a further object of the present invention to provide a method for the deodorizing and disinfecting of air which does not necessitate frequent changes of filter bed material.

It is a final object of the present invention to provide an apparatus for carrying out the method of the present invention.

In accordance with the above objects, the present invention utilizes a granular filter bed positioned in a conduit having an air flow therein. The conduit may be a portion of the air circulation system of an entire building, or may simply be associated with the air circulation of a single room. The granular filter bed may contain an adsorbent material such as activated carbon or simply a granular inert material. The granular filter bed is loaded with an oxidant and systems are provided for regenerating the oxidant loaded onto the granular filter bed.

In a first embodiment of the present invention, the oxidant is an oxidant-disinfectant such as iodine or chlorine. The oxidant is continuously regenerated by an ozone generator located upstream from the support bed. The capacity of the ozone generator is less than the peak regenerating requirements for the oxidant, and accordingly, the oxidant tends to become spent during peak periods. However, during low demand periods, such as during the night, the continuous flow of ozone into the oxidant tends to replenish the oxidant in anticipation of the peak periods. The above arrangement is advantageous because it results in a self contained system in which the oxidant is regenerated in situ. Accordingly, there is no need to gain access to the support bed for changing the filter materials thereof and the maintenance of the purification system is minimal. Further, the small size of the ozone generator eliminates the danger of high ozone concentrations which may be dangerous to ozone sensitive people or materials.

If the air space being deodorized and disinfected by the method and apparatus of this embodiment are subject to a minimal load for a period of time, the oxidant can become fully regenerated and permit unreacted ozone to pass through the support bed toward the outlet of the system whereby the ozone bearing air can enter the air volume being purified, thereby creating a potential hazard to ozone sensitive persons and materials. Accordingly, the apparatus of the present invention can include an excess zone detector located downstream from the support bed. The excess ozone detector may be connected to an ozone controller which provides a signal to a relay operated power switch for the ozone generator so that the ozone generator may be temporarily rendered inoperative when the ozone detector detects ozone at above a predetermined level.

The support material may be inert granular material or adsorbing type filter material such as activated charcoal. In the case of adsorbing type filtering material, the present invention provides the advantageous feature that a single filter element performs the functions of an activated carbon filter and an oxidizing filter bed. This permits economy in installation and maintenance. Alternatively, a single support may contain inert and adsorbing type granular material while the granular type material contained therein maybe either loaded or unloaded with oxidant. The adsorbent material will act more efficiently as an adsorbent if it is not already saturated with oxidant. As yet another alternative, two or more support beds maybe provided in series, some containing inert material loaded with oxidant while others contain unloaded adsorbent material such as activated carbon.

In a second embodiment, the oxidant is in the form of a water soluble chemical oxidant such as potassium permanganate or ammonium persulfate which cannot be regenerated by ozone. In this embodiment, the oxidant is dissolved in an aqueous solution and stored in an oxidant reservoir. The aqueous solution is supplied to the support bed and preferably permitted to dry. Once dried, the air flow maybe directed to the support bed for the purification thereof. Once the oxidant has become spent, it can be raised from the support bed and transported into a spent oxidant reservoir. Oxidant from the spent oxidant reservoir may be transported into an oxidant generator wherein the oxidant is electrolytically or chemically regenerated in a known manner. The oxidant, which has been regenerated "offline" may be then be returned to the oxidant reservoir for reuse.

In this second embodiment, it may be desirble to provide two sets of support beds in parallel conduits so that one end may be used while the other is being regenerated.

Each of the beds may contain a mixture of inert polar (hydrophilic) support material as well as adsorbent non-polar (hydrophobic) material. Under such circumstances, the oxidant would become loaded upon the inert material without being loaded upon and saturated or blinding the adsorbent material which may then adsorb the organic contaminants in the air stream. Alternatively, a series of support beds may be used each containing either inert or adsorbent support material.

In summary, the present invention provides a continuous, in situ, air purification system which deodorizes and disinfects an air stream without the need for frequent maintenance such as the need to change filter bed material, and without the introduction of unpleasant odors into the air stream. This is accomplished by an apparatus which is compact, self contained, and which can be manufactured relatively inexpensively.

BRIEF DESCRIPTION OF THE DRAWINGS

Various other objects, features and attendant advantages of the present invention will be more fully appreciated as the same become better understood from the following detailed description when considered in connection with the accompanying drawings in which like reference characters designate like or corresponding parts through the several views and wherein.

DETAILED DESCRIPTION OF THE PREFERRED EMBODIMENTS

The preferred embodiments of the present invention will now be described with reference to the attached figures. Although the description of the preferred embodiments refers to the return duct of a building ventilation system, the present invention applies equally well to any size or type of air recirculation system for an air volume.

Figure 1:
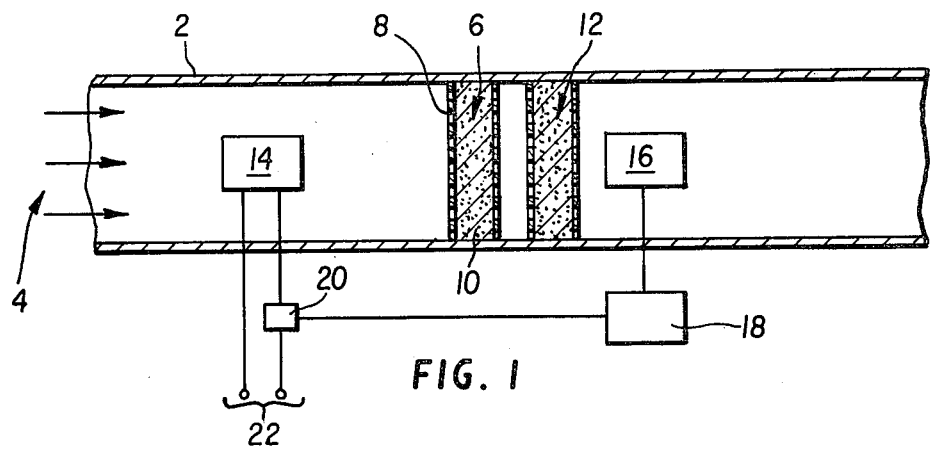
FIG. 1 is a schematic figure showing a first embodiment of the present invention.

Referring now to FIG. 1, there can be seen a return duct 2 for a building air recirculation system. Air transport means (not shown) such as blower fan located upstream or downstream from the apparatus of the present invention causes air to move through the conduit 2 in the direction of arrow 4. A support bed 6 is positioned in the conduit so as to completely fill a transverse cross section of the conduit 2 whereby no air can pass through the conduit without passage through the support bed 6. The support bed 6 consists of a pair of perforated elements 8, such as screens or porous sheets, with a bed of granular support material 10 located therebetween. The granular support material can be an inert granular material such as alpha alumina or granular adsorbent material such activated carbon. Alternatively, the support material may be a mixture of inert and adsorbent materials. As yet another alternative, a pair of serially located support beds 6 and 12 may be positioned within the conduit; one of the serial support beds may contain inert support material while the other contains an active adsorbent material, or one or the other of the beds may contain a combination of inert and adsorbent granular material.

An ozone generator 14 is positioned in the conduit at a point upstream from the support beds. Ozone generators, per se, are well known in the art and the precise structure of the ozone generator will not be herein described. Similarly, an ozone detector 16, the structure of which is also well known in the art, is positioned within the conduit 2 at a location downstream from the support beds. The ozone detector 16 is connected to control circuitry 18 of a known type which provides a signal to the relay switch 20 in response to a signal from the detector 16. The relay switch 20 is operatively associated with the line voltage 22 of the ozone generator, and can open to deactivate the ozone generator upon the receipt of a signal from the control circuit 18. Although the relay switch 20 is shown in the present embodiment, any other desirable means may be provided for deactivating the ozone generator upon receipt of a signal from the control circuit.

In operation, all of the support material is loaded with an oxidant-disinfectant such as iodine or chlorine; alternatively, where there are both active and adsorbent support materials, either in the same or serially arranged support beds, only the inert granular support material is loaded with the oxidant. Once this is done, the system may be placed into operation without the necessity of renewing or replacing the oxidant or the support material on a frequent maintenance basis.

Appropriate blower means (not shown) provide an air flow 4 through the conduit and past the support bed or beds. The ozone generator located upstream from the support bed or beds discharges a continuous supply of ozone to the air stream. The ozone generator is located sufficiently upstream from the first support beds so that the ozone can be substantially evenly distributed throughout the cross section of the conduit prior to reaching the first support beds. The ozone generator is of such a size that it produces significantly less ozone than is necessary for the regeneration of the oxidant during peak use. Accordingly, during such peak use periods the oxidant becomes gradually depleted, but at a rate less than that which would occur where no ozone is being supplied thereto.

The ozone generator 14 is also sized so that it provides substantially more ozone capacity than is required during anticipated low use, such as at night when few odors are being produced. Accordingly, due to the continuous operation of the ozone generator, the oxidant continues to absorb the ozone and be regenerated by a chemical reaction which is well known to those skilled in the art. Accordingly, although ozone is produced in the air stream of a building air recirculation conduit, this ozone is consumed by the oxidant during both peak and low demand times for the regeneration of the oxidant so that the ozone level in the rooms being ventilated is not substantially raised and unpleasant or dangerous ozone odors will not be perceived by the persons in these rooms nor will the ozone harm sensitive materials such as drapery fabric dyes. The small size of the ozone generator is of significant importance since the small size, together with the continuous operation of the generator results in a gradual application of ozone which can be effectively absorbed by the oxidant, and which can be detected and discontinued in the case of failure of the oxidant to absorb the ozone, without the danger of a large dose of ozone being circulated into the room before steps can be taken for the deactivation of the ozone generator.

During the use of the above embodiment, the oxidant absorbs odors and becomes spent in a well known manner. Further, if unloaded adsorbent granular material is present in the support beds, this unloaded adsorbent material will adsorb odors. Accordingly, a single filter element performs the functions of both an activated carbon filter and an oxidizing filter bed. This permits economy in installation and maintenance of the apparatus. Further, because of the continuous regeneration of oxidant the need for frequent changes of the filter bed material is reduced or eliminated. A further advantage of the present invention is that the chemical oxidant destroys infectious agents which might accumulate on the chemically inert but adsorbent filter material. Finally, the regeneration of the oxidant is in situ so that it is not necessary to gain access to the support bed in order to provide for the regeneration thereof.

Figure 2:
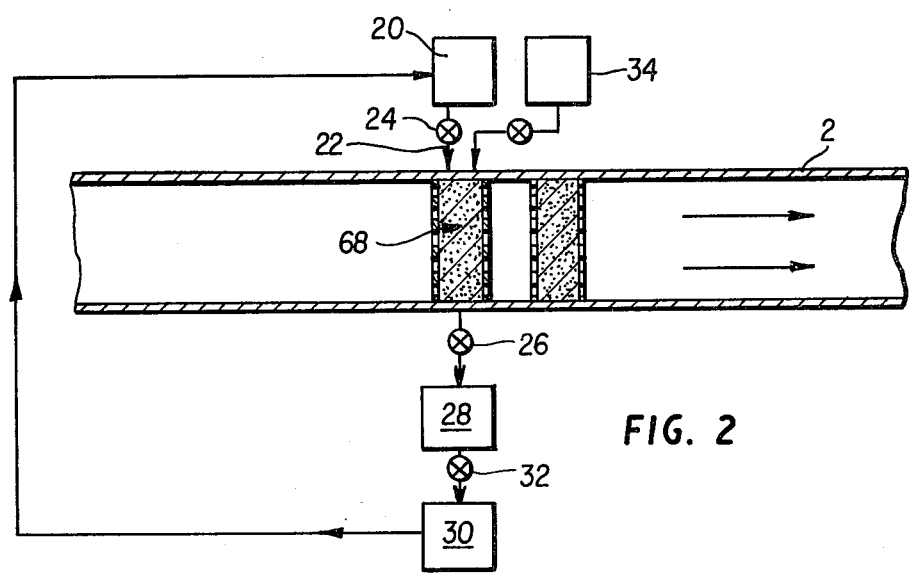
FIG. 2 is a schematic figure showing a second embodiment of the present invention.

A second embodiment of the present invention is found in FIG. 2. In this embodiment, a conduit, blower means, and one or more support beds are provided as in the embodiment of FIG. 1. However, in this embodiment a non-volatile, water soluble, chemical oxidant such as potassium permanganate or ammonium persulfate is dissolved into a dilute aqueous solution. This aqueous solution is placed in an oxidant reservoir 20 which is connected to the support bed 8 by conduit 22. A valve or similar flow control apparatus may be associated with the conduit 22 for selectively permitting the flow of the aqueous solution from the reservoir 20 into the support bed 6. The flow of solution into the support bed can be accomplished either by gravity or through the use of suction or positive pressure provided by a pump.

A conduit 26 including a valve or similar flow control means connects the support bed to a spent oxidant reservoir 28. The spent oxidant reservoir collects spent oxidant in preparation for transport to the electrolytic or chemical regenerator 30 via a conduit and valve or similar flow control apparatus 32. The electrolytic or chemical regenerator includes a source of electrical energy or chemical regeneration substances which provide chemical or electrolitic regeneration of the spent oxidant solution in a manner well known to those skilled in the art. Once the oxidant has been regenerated in regenerator 30, it is transported back to the oxidant reservoir 20 by a pump (not shown).

As in the embodiment of FIG. 1, one or more additional support beds may be placed within the conduit at positions upstream or downstream from the support bed receiving the oxidant. These additional support beds preferably contain an adsorbtion type support material which adsorbs additional odors which were not oxidized by the oxidant in support bed 6.

A water reservoir 34, including a conduit and flow control valve therefor, are connected to the support bed 6 and supply rinsing fluid to the support bed.

In use, the oxidant containing aqueous solution is permitted to drain into, and saturate, the support bed 6. The flow of aqueous solution is subsequently shut off and the air flow within the conduit 2 is activated for the transport of deodorized and disinfected air into the rooms associated with the conduit 2. Alternatively, the air flow can be diverted until the aqueous solution has evaporated so that a dry non-volatile oxidant is loaded on a dry support bed. As yet another alternative, the system can remain in a deactivated condition, such as during a low use period, in order to permit the aqueous solution to dry.

Once the air recirculation system has been operative for a predetermined time, which can be determined by those skilled in the art through routine experimentation, the oxidant will have become substantially spent. At that time, an aqueous rinsing solution from reservoir 34 can be permitted to flow into the support bed 6, either through gravity or by a pump (not shown) for rinsing the oxidant from the support bed. The rinse containing the spent oxidant is then permitted to flow through conduit 26 into the spent oxidant reservoir. The spent oxidant solution can then be immediately transported into the electrolytic or chemical regenerator 30, or alternatively the spent oxidant can be stored in the spent oxidant reservoir while subsequent charges of fresh oxidant are introduced into the support bed, become spent, and are subsequently transported into the spent oxidant reservoir.

When a desired quantity of spent oxidant solution has accumulated in the spent oxidant reservoir, the solution is permitted to drain via conduit 32 into the electrolytic or chemical regenerator 30 where it is regenerated in a well known manner. The regenerated oxidant solution is subsequently transported, as by pumping, back to the oxidant reservoir 20 where it is available for further use in the support bed.

Where the support bed contains a mixture of inert and adsorbent support material, it is desirable to use a hydrophilic polar support material as the inert material and a polar hydrophobic support material as the adsorbent material. Accordingly, the oxidant containing aqueous solution will adhere only to the polar hydrophilic inert support material and not to the hydrophobic adsorbent material. Therefore, the adsorbent material will not become "blinded" by the oxidant and will be able to efficiently function to adsorb the organic contaminants in the air stream in a manner complementary to the oxidant purification.

Figure 3:
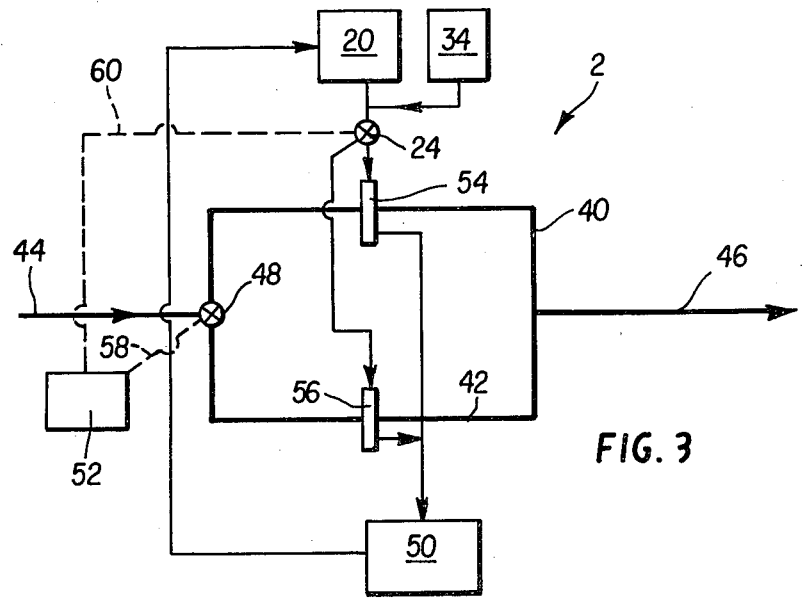
FIG. 3 is a schematic diagram showing a variation of the second embodiment of the present invention.

FIG. 3 is a diagrammic representation of a variation of the second embodiment in which the conduit 2 is divided into a pair of parallel conduit sections 40 and 42 connected on the upstream side by a conduit portion 44 and on the downstream side by a conduit portion 46. A valve 48 is provided for selectively directing air flow to either conduit portion 40 or conduit portion 42. Elements 20 and 34 are the oxidant reservoir and aqueous rinsing solution reservoir, respectively, as in FIG. 2 while element 50 represents a composite of the spent oxygen reservoir and electrolitic or chemical regenerator. A control circuit 52 controls the operation of valve 48 as well as valve 24 which directs oxidant into either support bed 54 or 56.

By use of this variation of the second embodiment, it is possible to selectively use one support bed for air purification while the other support bed is being regenerated and dried. The control circuit 52 can, for example, selectively direct air flow into conduit section 40 for a predetermined time period. During that time, the control circuit can operate the valve 24 in a manner to direct aqueous rinsing fluid into the support bed 56, followed by aqueous oxidant solution. Appropriate support valves, similar to those of FIG. 2, are provided for controlling the flow of liquid through the various lines in a manner similar to that of the embodiment of FIG. 2. Once the support bed 56 has become saturated with oxidant solution, the support bed 56 may remain in an inoperative condition until the oxidant in support bed 54 has become spent, during which time the aqueous solution in support bed 56 can dry so as to leave a dry support bed fully loaded with oxidant.

After the predetermined time period for the operation of the support bed 54, which may be set by a clock associated with the control circuit 52, the control circuit switches valve 48 and 24, via lines 58 and 60, respectively, which may be either electric or hydraulic, so that the air flow is directed through the conduit section 42 and the aqueous solutions are directed through the filter bed 54 so as to rinse and recharge the oxidant in the filter bed 54. Accordingly, a continuous air purification system may be provided which need not be temporarily shut down for the recharging and regeneration of the filter beds with water soluble oxidants.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for disinfecting and deodorizing the air of inhabitable enclosures, comprising the steps of:
   passing a stream of said air in a flow direction through conduit means;
   positioning at least one bed of support material in said conduit means, said support material being at least one from the group consisting of chemically inert granular material and adsorbing type filter material;
   loading an oxidant from the group consisting of iodine and chlorine on said at least one bed of support material;
   introducing ozone into said air stream at a first point upstream from said at least one bed of support material, whereby said air stream is purified by said ozone and said oxidant on said support material and whereby said oxidant on said support material is regenerated by said ozone;
   providing means in said air stream at a second point downstream from said at least one bed of support material and prior to returning the air stream to the enclosure for detecting the ozone concentration at said second point and;
   terminating said ozone introduction when the concentration of ozone at said second point exceeds a predetermine level, whereby the build up of ozone in said enclosure is prevented.

2. The method of claim 1 wherein said regeneration is substantially continuous.

* * * * *